(12) United States Patent
Brown et al.

(10) Patent No.: US 10,361,009 B2
(45) Date of Patent: Jul. 23, 2019

(54) SYSTEM AND METHOD FOR MULTI-SIDED, INTENSITY-MODULATED IRRADIATION OF A PRODUCT

(71) Applicant: MEVEX CORPORATION, Stittsville (CA)

(72) Inventors: Peter W. A. Brown, Almonte (CA); David A. Brown, Dunrobin (CA); David J. Hepworth, Ottawa (CA); David Macrillo, Almonte (CA)

(73) Assignee: MEVEX CORPORATION, Stittsville (CA)

( * ) Notice: Subject to any disclaimer, the term of this patent is extended or adjusted under 35 U.S.C. 154(b) by 233 days.

(21) Appl. No.: 15/205,579

(22) Filed: Jul. 8, 2016

(65) Prior Publication Data

US 2017/0040080 A1    Feb. 9, 2017

Related U.S. Application Data

(60) Provisional application No. 62/189,997, filed on Jul. 8, 2015.

(51) Int. Cl.
*G01N 23/00*    (2006.01)
*G21K 5/10*    (2006.01)

(52) U.S. Cl.
CPC ......... *G21K 5/10* (2013.01); *G01N 2223/643* (2013.01)

(58) Field of Classification Search
CPC ........................... G21K 5/10; G01N 2223/643
See application file for complete search history.

(56) References Cited

U.S. PATENT DOCUMENTS

| | | | |
|---|---|---|---|
| 6,504,898 B1 * | 1/2003 | Kotler | G21K 5/04 378/64 |
| 2003/0155526 A1 * | 8/2003 | Woodburn | G21K 5/04 250/453.11 |

* cited by examiner

*Primary Examiner* — Dani Fox
(74) *Attorney, Agent, or Firm* — Borden Ladner Gervais LLP; Louis B. Allard

(57) ABSTRACT

A system and method for irradiating a product in order to obtain an irradiated product that has a suitable irradiation dose uniformity ratio and is less expensive and faster than existing systems. The system includes a controller that varies the speed at which a product to be irradiated is moved across a radiation beam. The speed is varied in accordance with a speed function that can be a quadratic function of the distance between a position at which the surface of the product is irradiated and a reference position.

12 Claims, 11 Drawing Sheets

SYSTEM AND METHOD FOR MULTI-SIDED, INTENSITY-MODULATED IRRADIATION OF A PRODUCT

FIELD

The present disclosure relates generally to particle accelerators. More particularly, the present disclosure relates to a particle accelerator system and method for irradiating a product.

BACKGROUND

Irradiation of products, whether they are food products or medical devices, is known in the art. The delivery of a sufficient minimum radiation dose is required to ensure efficacy of the process and compliance with regulations. The ability to maintain the radiation dose below a maximum value is required to avoid damage to the processed product and/or to remain below prescribed regulatory maxima for radiation doses.

Irradiation of products with an irradiation dose that is uniform, to a certain degree, on and within surfaces of a given product is also known. The ratio of maximum dose to minimum dose is referred to as the dose uniformity ratio (DUR). In some prior art uniform dose irradiation systems, steel shutters and an x-ray beam are used to irradiate, one after the other, the surfaces of a product that is conveyed across the x-ray beam multiple times for each of the surfaces. The steel shutters are used to attenuate different widths of the x-ray beam each time the product is conveyed across the x-ray beam in order to obtain a final irradiated product that has received a uniform irradiation dose of x-rays. This is done to achieve a constant DUR for each portion of each surface of the product.

Such prior art systems require multiple passes of the product across the x-ray beam and are inefficient in that they waste a considerable amount of x-ray radiation through the irradiation of the steel shutters during the multiple passes of the product across the x-ray beam.

Therefore, improvements in systems and methods for the irradiation of products are desirable.

SUMMARY

It is an object of the present disclosure to obviate or mitigate at least one disadvantage of previous prior art systems.

In a first aspect, the present disclosure provides a system for irradiating a product. The system comprises a radiation source to generate a radiation beam; a conveyor to move the product across the radiation beam to expose a surface of the product to the radiation beam in order to irradiate the surface; and a controller to control a speed at which the conveyor moves the product across the radiation beam. The speed is a function of a distance between a position at which the surface of the product is irradiated and a reference position.

In a further embodiment, there is provided a method of irradiating a product. The method comprises: conveying a product across a radiation beam to expose a surface of the product to the radiation beam; and controlling a speed at which the product is conveyed across the radiation beam. The speed is a function of a distance between a position at which the surface of the product is irradiated and a reference position.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Generally, the present disclosure provides a system and method to irradiate a product with a substantially uniform irradiation dose, which reduces the DUR value of the irradiated product. The substantially uniform irradiation dose is attained by conveying the product across the path of a radiation beam (e.g., an electron beam or an x-ray beam) at a conveyor speed that varies as function of the position of the product with respect to the radiation beam. As an example, the conveyor speed function can be a quadratic function of the position of the product with respect to the radiation beam. Multiple faces or sides of the product can be exposed, in sequence (i.e., one after the other), to the radiation beam. For each surface, the product is conveyed across the radiation beam at a conveyor speed that varies as a function of the position of the product with respect to the x-ray beam. The conveyor speed function effectively modulates or controls the dose of radiation delivered to the product. Any suitable type of product can be irradiated. Examples of such product include food, e.g., produce, and medical devices.

The present disclosure improves the efficiency, accuracy, and throughput of radiation processing of products by reducing the wasted ionizing energy delivered to the surfaces of products and by improving the DUR.

Figure 1:
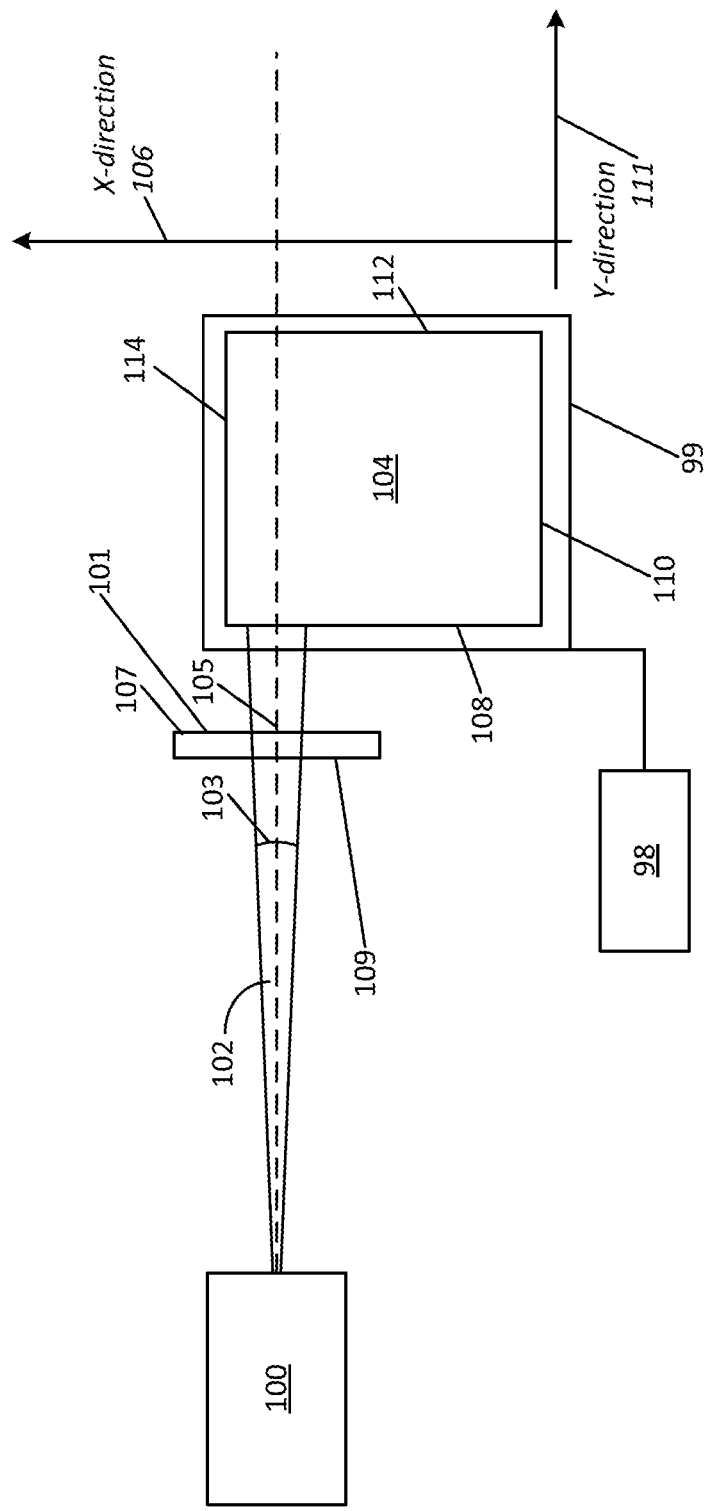
FIG. 1 shows an embodiment of an X-ray irradiation system in accordance with the present disclosure.

FIG. 1 shows a block diagram representation of an embodiment of a system for multi-sided, intensity modulated irradiation of a product in accordance with the present disclosure. The system includes a radiation source 100 providing a radiation beam 102 to a product 104. The radiation beam 102 can be an electron beam, and x-ray beam, or any other suitable type of radiation beam. The radiation beam 102 is spread over an angle 2Ø, shown at reference numeral 103. The radiation beam is typically scanned in the z-direction i.e., perpendicularly to the x and y directions, along a height of the product being irradiated. The scanning in the z-direction can be controlled to deliver a substantially constant radiation dose to the product along the z-direction.

As will be understood by the skilled worker, to enable x-ray irradiation, an electron source can be selected as the radiation source 100 to generate an electron beam and, an electron to x-ray converter (a bremsstrahlung converter) plate 107 can be placed between the radiation source 100 and the product 104. The output side 101 of the converter plate 107 radiates x-rays in a characteristic pattern along the same direction as the impinging electrons on the input side 109 of the converter plate 107.

To irradiate the product 104, a conveyor 99 moves (conveys) the product 107 across the path of the radiation beam 102, along the x-direction 106, which is perpendicular to the central axis of 105 of the radiation beam 102. In a first pass across the radiation beam 102, the surface 108 of the product is irradiated. Subsequently, the product 104 is rotated by 90 degrees clockwise and the product is again conveyed along the x-direction 106 to irradiate the surface 110 of the product. Following irradiation of the surface 110, the product is again rotated by 90 degrees and conveyed in the x-direction 106 to irradiate the surface 112. Finally, the product is further rotated by 90 degrees and is conveyed in the x-direction 106 to irradiate the surface 114. As will be understood by the skilled worker, additional surfaces or fewer surfaces of the product can be irradiated without departing from the scope of the present disclosure. The y-direction is shown at reference numeral 111.

A conveyor controller system 98 controls the speed of the conveyor 99. The conveyor 99 can include any suitable type of motor or actuator or any other type of displacement mechanism that can act to move the product 104 along a linear direction; the conveyor can include elements to allow the conveyor to rotate, lift, or rotate and lift, the product 104. The conveyor controller system 98 can include a processor and a computer-readable medium that has recorded thereon instructions to be carried out by the processor to control the motor or actuator or any other type of displacement mechanism to move the product 104.

Figure 2:
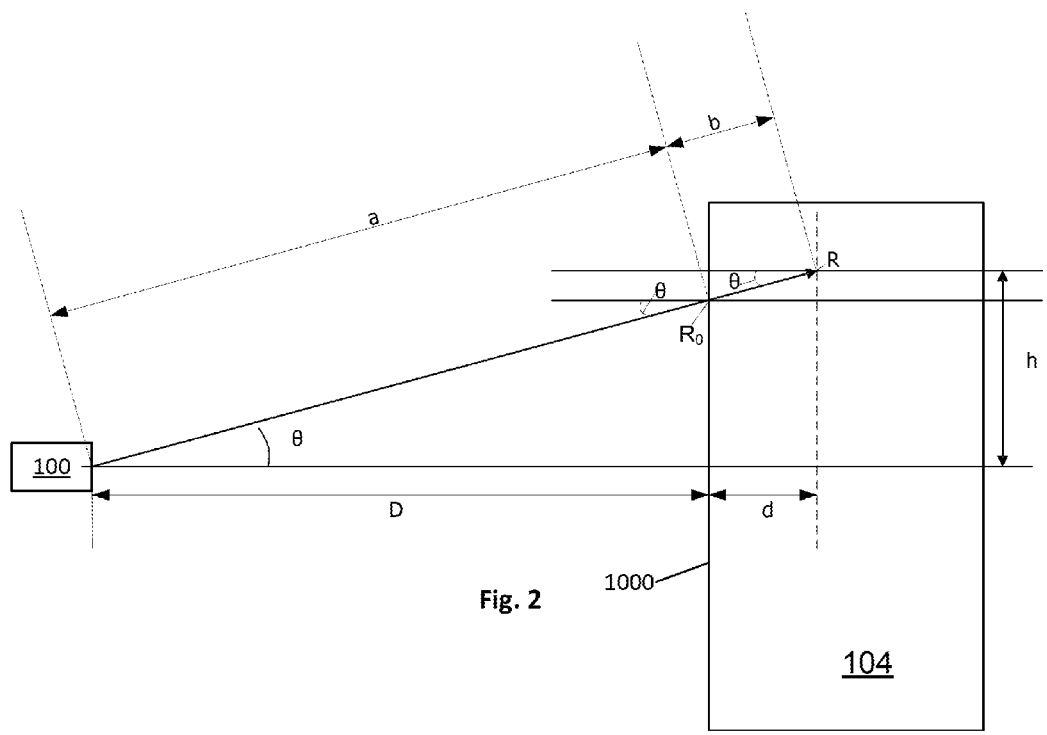
FIG. 2 shows geometrical aspects of an irradiation system in accordance with embodiments of the present disclosure.

With reference to FIG. 2, for irradiation stemming directly from a radiation source, for example, the aforementioned radiation source 100, when the conveyor speed along the x-direction 106 is constant, the resulting irradiation dose (Dose$_d$) at point 'R', which is at a depth 'd' from a surface (surface 108, 110, 112, or 114) and at an angle θ from the radiation source can be calculated using the following equation:

$$\text{Dose}_d = \text{Dose}_0 \times \frac{1}{(a+b)^2} \times e^{-100\mu b \rho} \quad \text{(equation 1)}$$

where Dose$_0$ is the irradiation dose received directly at the point 'R$_0$' on the surface 1000, $$\theta = \tan^{-1}\left(\frac{h}{D+d}\right), a = \frac{D}{\cos\theta}, \text{ and } b = \frac{d}{\cos\theta}.$$

'D' is the distance between the irradiation source 100 and the surface 1000, 'd' is the depth for which the dose is calculated, and 'h' is the vertical distance from the irradiation source 100 to the point 'R'. Further, μ is the mean mass attenuation coefficient of the product being irradiated by the radiation stemming from the irradiation source and ρ is the mean density of the product 104 being irradiated.

Figure 3:
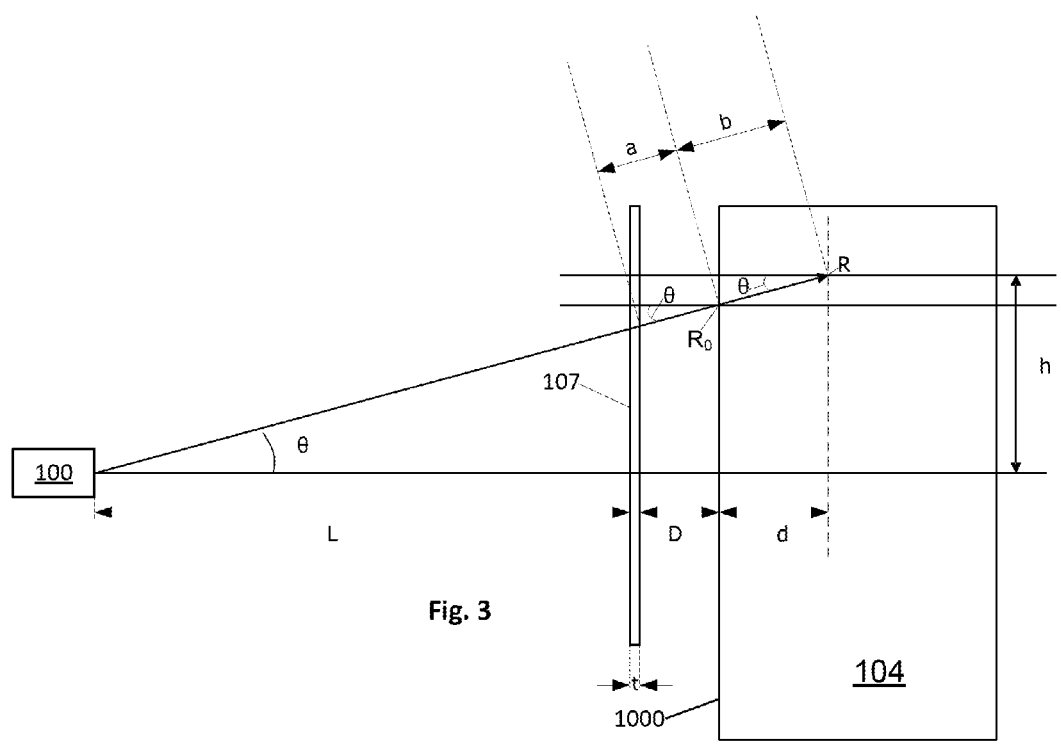
FIG. 3 shows geometrical aspects of an X-ray irradiation system in accordance with embodiments of the present disclosure.

In another example, FIG. 3 shows the product 104 being irradiated not directly from the irradiation source 100 but is instead from an x-ray converter plate 107 that is itself irradiated directly from the irradiation source 100. In this case, the resulting irradiation dose (xDose$_d$) at point 'R', which is at a depth 'd' from the surface 1000 and at an angle θ from the radiation source can be calculated using the following equation:

$$x\text{Dose}_d = x\text{Dose}_0 \times \frac{1}{(a+b)^2} \times e^{-100\mu b \rho} \quad \text{(equation 2)}$$

where xDose$_0$ is the irradiation dose received directly at the point 'R$_0$' on the surface 1000, $$\theta = \tan^{-1}\left(\frac{h}{L+t+D+d}\right), a = \frac{D}{\cos\theta}, \text{ and } b = \frac{d}{\cos\theta}.$$

'L' is the distance between the irradiation source 100 and the x-ray converter plate 107, 't' is the thickness of the x-ray converter plate 107, 'D' is the distance between the x-ray converter plate and the surface 1000, 'd' is the depth for which the dose is calculated, and 'h' is the vertical distance from the irradiation source 100 to the point 'R'. Further, μ is the mean mass attenuation coefficient of the product being irradiated by the x-rays stemming from the x-ray converter plate 107 and ρ is the mean density of the product 104 being irradiated.

Figure 4:
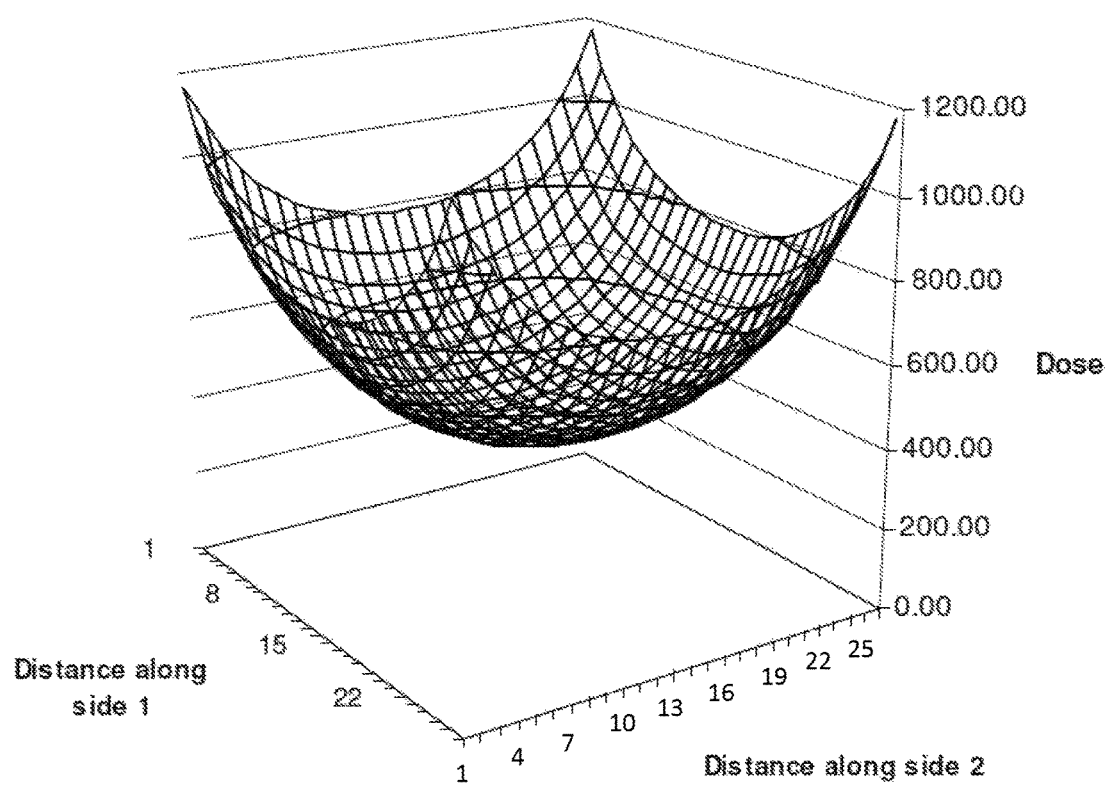
FIG. 4 shows an irradiation dose profile in accordance with the prior art.

FIG. 4 shows an example of an irradiation dose profile for the product 104 when the product 104 (shown in FIG. 1) is moved a constant speed across the beam 102 (shown in FIG. 1). In this figure, side 1 can be considered to be surface 108 (shown at FIG. 1) and side 2 can be considered to be surface 110 (shown at FIG. 1). As evidenced by FIG. 4 there is a higher dose at the edges of the product than at the center. In this example, the dose uniformity ratio (DUR) is about 6.3:1.

Figure 5:
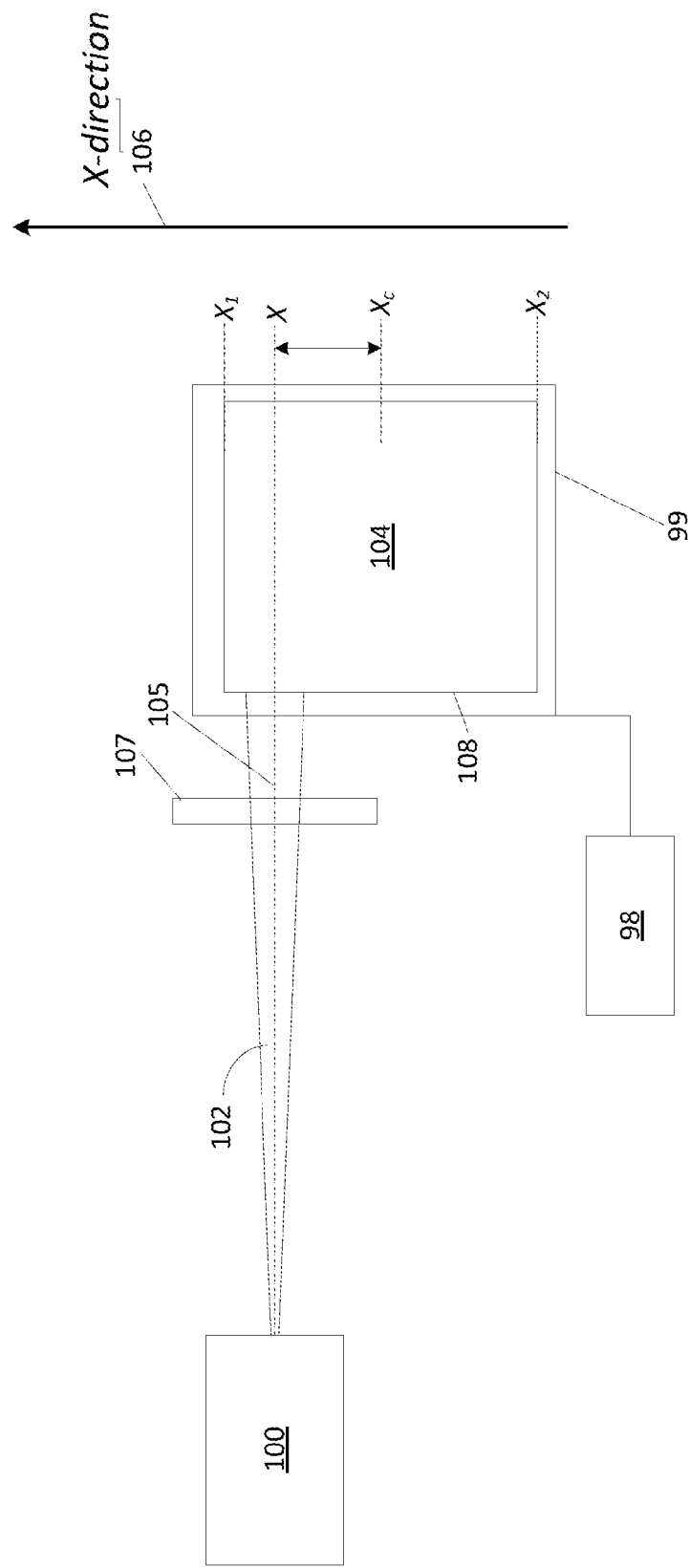
FIG. 5 shows the embodiment of FIG. 1 with exemplary position coordinates on the product being irradiated.

The inventors have discovered that by varying the speed at which the product 104 is conveyed across the beam, that an improved DUR can be obtained. As an example, instead of the product 104 being conveyed across the beam 102 at constant speed, conveying the product 104 at a speed that is a quadratic function of the distance between the beam and the center of the product 104 can produce an improved DUR. As an example of such a quadratic function, the speed of conveying the product 104 across the radiation beam 102 can be set in accordance with the speed function (SF):

$$SF(x) = 2.45 * x^2 - 2.7 * x + 0.905 \quad \text{(equation 3)}$$

where 'x' is equal to the difference between the x-coordinate at which the product is being irradiated and 'x$_c$', which is the center of the side of the product being irradiated. This is represented at FIG. 5 where 'x$_1$' is at one edge of the product and 'x$_2$' is at the opposite edge. In this embodiment, the conveyor controller system 98 is configured to move the product in accordance with the speed function of equation 3. That is, the computer-readable medium of the conveyor controller system 98 has recorded thereon instructions to be carried out by the processor of the conveyor controller system 98 to control the motor or actuator or any other type of displacement mechanism to move the product 104 in accordance with the speed function of equation 3.

Figure 6:
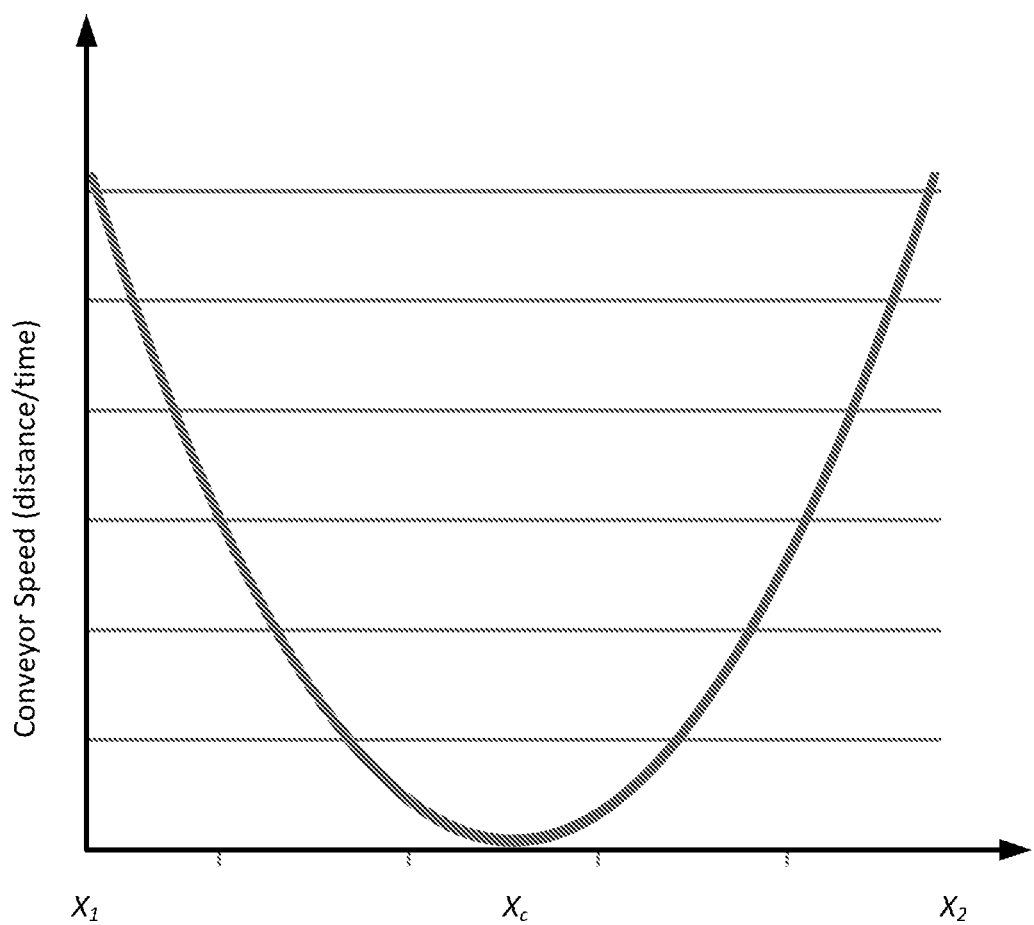
FIG. 6 shows an example of a quadratic speed function in accordance with an embodiment of the present disclosure.

FIG. 6 shows a plot of the speed at which product 104 is conveyed across the radiation beam 102 as a function of '$x-x_c$'. The speed is greater when the product 104 is irradiated near '$x_1$' or '$x_2$' than when the product is irradiated at position '$x_c$'. Essentially, the conveyor speed is reduced as the product 105 goes from being irradiated at the edge '$x_1$' to being irradiated at the center '$x_c$' and then, the conveyor speed is increased as the product is conveyed to be irradiated at the edge '$x_2$'.

Figure 7:
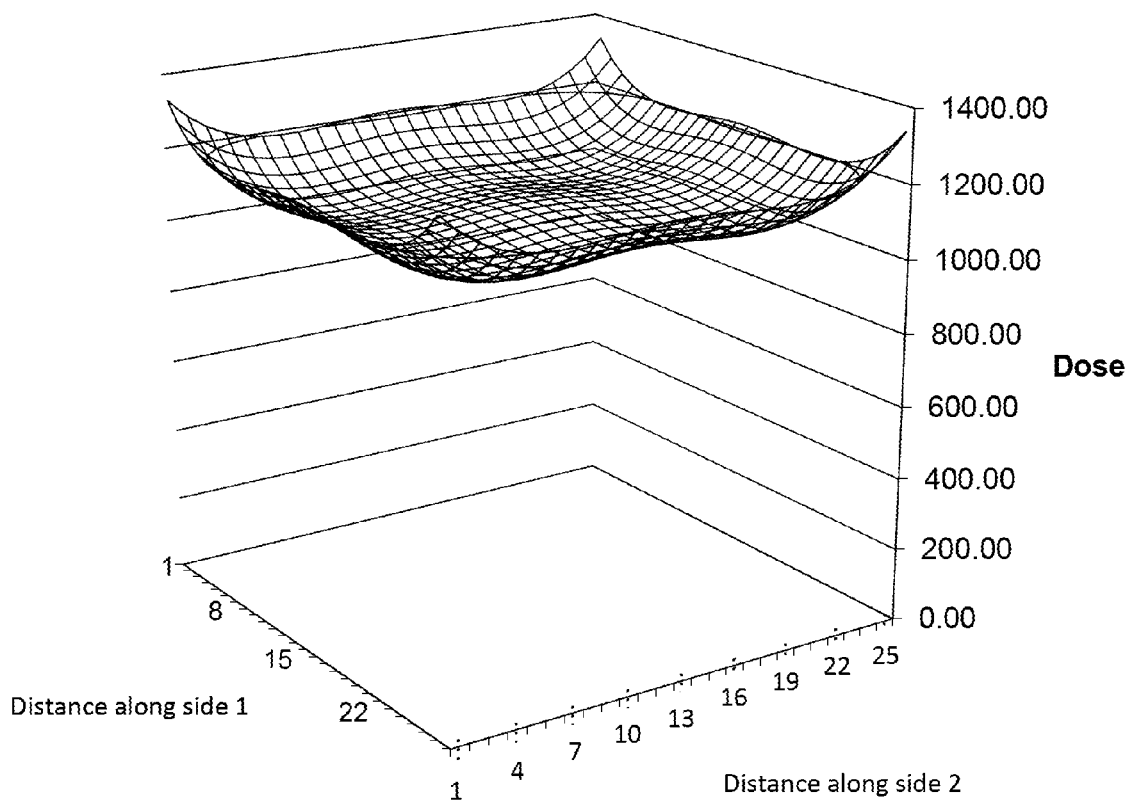
FIG. 7 shows an irradiation dose profile in accordance with an embodiment of the present disclosure, for a product having a mean density of 0.8 g/cm$^3$.

By irradiating each side of the product 105 in accordance with the conveyor speed function of equation 3, the uniformity of the irradiation dose delivered and, the DUR is improved as evidenced by FIG. 7 where the DUR, in this example, is about 1.22:1. In the example of FIG. 7, the mean product density is 0.8 g/cm$^3$.

Even though equation 3 is a quadratic speed function, any other type of speed function is to be considered within the scope of the present disclosure. For example, the polynomial speed function of equation 4 below is also within the scope of the present disclosure.

$$SF(x)=a_n x^n+a_{n-1}x^{n-1}+\ldots+a_2 x^2+a_1 x+a_0 \quad \text{(equation 4)}$$

with 'n' being a positive integer and '$a_i$' being the polynomial coefficients.

Figure 8:
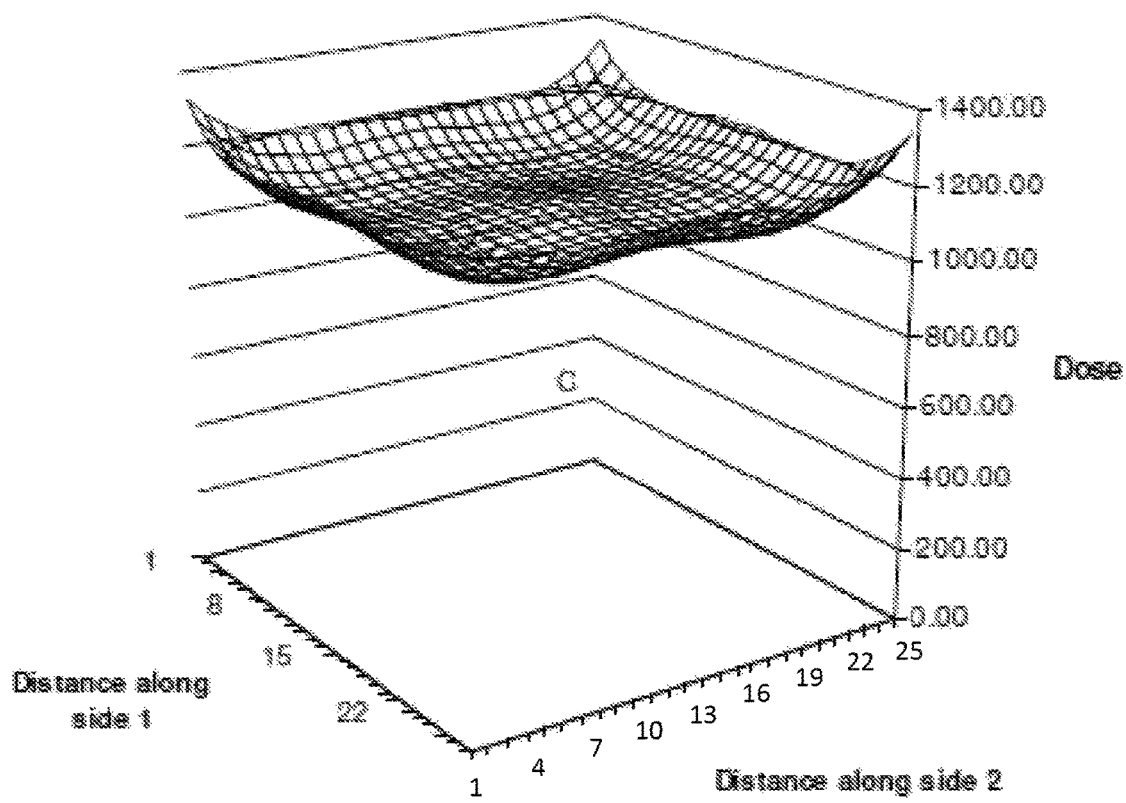
FIG. 8 shows an irradiation dose profile in accordance with an embodiment of the present disclosure, for a product having a mean density of 0.2 g/cm$^3$.
Figure 9:
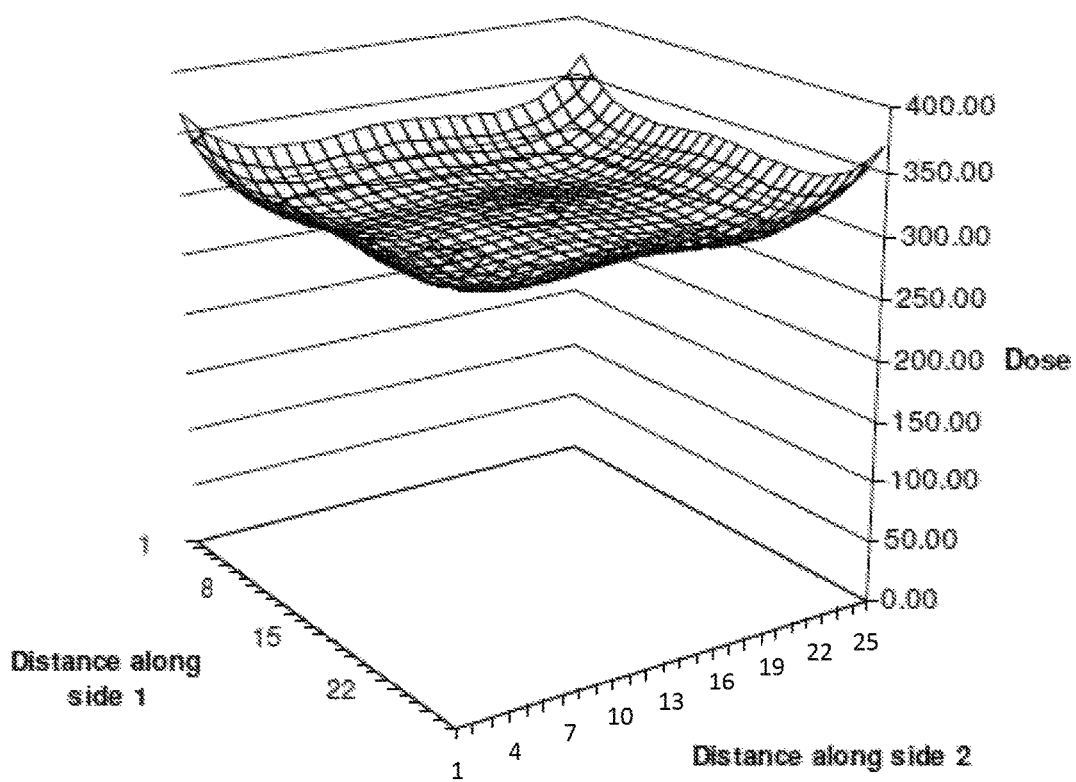
FIG. 9 shows an irradiation dose profile in accordance with an embodiment of the present disclosure, for a product having a mean density of 0.4 g/cm$^3$.
Figure 10:
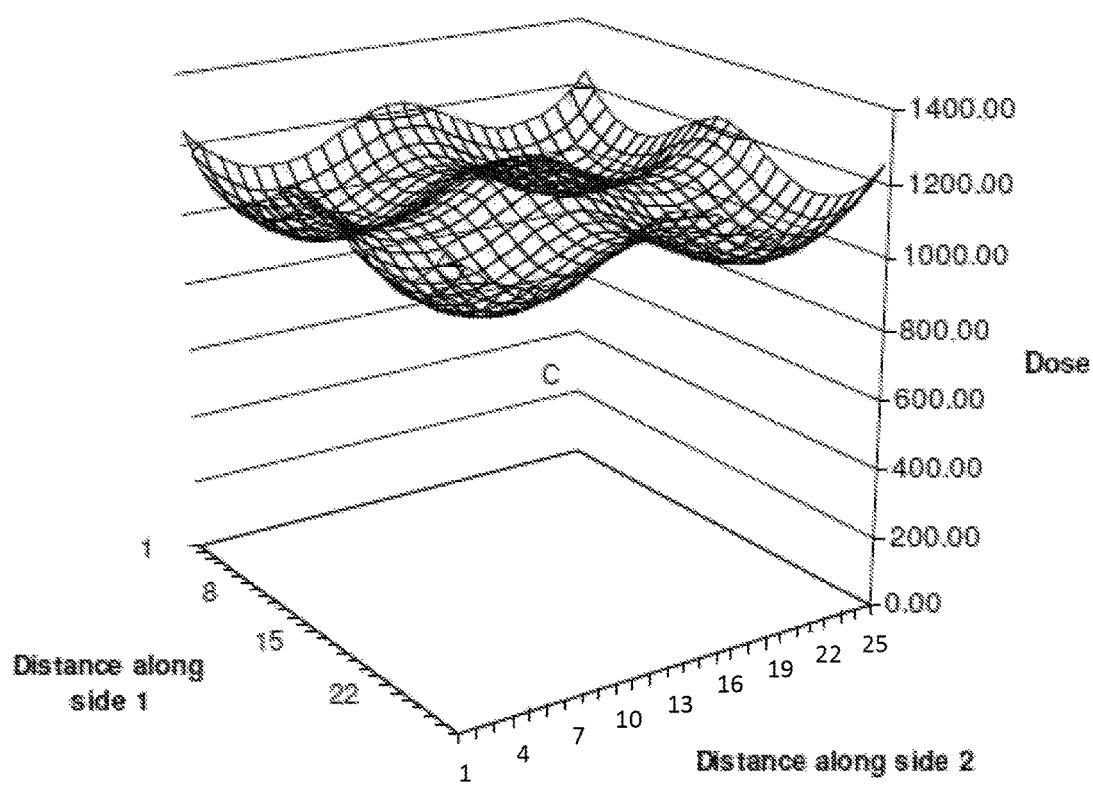
FIG. 10 shows an irradiation dose profile in accordance with an embodiment of the present disclosure, for a product having a mean density of 0.6 g/cm$^3$.

As will be understood by the skilled worker, the polynomial coefficients '$a_i$' can be obtained by radiation simulations. FIGS. 8, 9 and 10 show examples of quadratic coefficients of the speed control function for different speed function and mean product densities. In these examples, x-ray radiation is used to irradiate the product.

In the example of FIG. 8, the mean product density is 0.2 g/cm$^3$ and the speed function is:

$$SF(x)=x^2-1.5*x+0.905 \quad \text{(equation 5)}$$

This produces a DUR=1.265. In the example of FIG. 9, the mean product density is 0.4 g/cm$^3$ and the speed function is:

$$SF(x)=1.9*x^2-2.2*x+0.905 \quad \text{(equation 6)}$$

This produces a DUR=1.248. In the example of FIG. 10, the mean product density is 0.8 0.6 g/cm$^3$ and the speed function is:

$$SF(x)=1.97*x^2-2.4*x+0.905 \quad \text{(equation 7)}$$

This produces a DUR=1.284.

Even though the examples above are for products having flat surfaces, the irradiation of products having arbitrarily shaped surfaces is to be considered within the scope of the present disclosure. Further, in the aforementioned examples, only four of the six sides of the product are irradiated. This need not be the case. The irradiation of any number of total number of surfaces is to be considered within the scope of the present disclosure.

Figure 11:
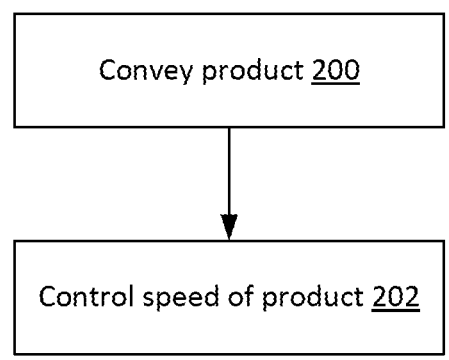
FIG. 11 shows a flowchart of an embodiment of a method of the present disclosure.

FIG. 11 shows a flowchart of an embodiment of a method in accordance with the present disclosure. At action 200, a product secured to a conveyor is conveyed across a radiation beam to irradiate a surface of the product. At action 202, the speed of the conveyor to which the product is secured is varied in accordance with a position of the product with respect to the radiation beam. As will be understood by the skilled worker, any suitable known technique can be used to detect the edges of the product to be irradiated. Further, any suitable type of conveyor can be used to maintain a proper orientation of the product during irradiation.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A system for irradiating a product, the system comprising:
    a radiation source to generate an x-ray beam;
    a conveyor to move the product in a linear direction across the x-ray beam as the product is being irradiated, to expose a surface of the product to the x-ray beam in order to irradiate the surface; and
    a controller coupled to the conveyor, the controller configured to vary a speed at which the conveyor moves the product in the linear direction across the x-ray beam as the product is being irradiated, the speed being a function of a distance between a position at which the surface of the product is irradiated and a reference position on the surface of the product, the controller being configured to reduce the speed at which the conveyor moves the product as the position at which the surface is being irradiated becomes closer to the reference position, the controller being further configured to increase the speed at which the conveyor moves the product as the position at which the surface is being irradiated becomes farther from the reference position.

2. The system of claim 1 wherein the conveyor is configured to rotate the product to expose, sequentially, additional surfaces of the product to the x-ray beam.

3. The system of claim 2 wherein the controller is configured to vary the speed at which the conveyor moves the product in the linear direction across the x-ray beam to expose the surface and the additional surfaces to obtain an irradiated product that has a dose uniformity ratio (DUR) that meets a target DUR.

4. The system of claim 1 wherein the controller is configured to vary the speed of the conveyor in the linear direction in accordance with a speed function, the speed function being a quadratic function of the distance between the position at which the product is irradiated and the reference position.

5. The system of claim 4 wherein the reference position is a center position of the surface being irradiated.

6. The system of claim 1 wherein the controller is configured to vary the speed of the conveyor in the linear direction in accordance with a speed function, the speed function being a polynomial function of the distance between the position at which the surface of the product is irradiated and the reference position.

7. The system of claim 4 wherein the reference position is a center position of the surface being irradiated.

8. A method of irradiating a product, the method comprising:
conveying a product in a linear direction across an x-ray beam to expose a surface of the product to the x-ray beam as the product is conveyed in the linear direction; and
varying a speed at which the product is conveyed in the linear direction across the x-ray beam as the product is being irradiated, the speed being a function of a distance between a position at which the surface of the product is irradiated and a reference position on the surface, the varying of the speed being to reduce the speed at which the conveyor moves the product as the position at which the surface is being irradiated becomes closer to the reference position, the varying of the speed further being to increase the speed at which the conveyor moves the product as the position at which the surface is being irradiated becomes farther from the reference position.

9. The method of claim 8, wherein the conveyor is configured to rotate the product, the method further comprising the conveyor rotating the product to expose, sequentially, additional surfaces of the product to the x-ray beam.

10. The method of claim 9 further comprising:
determining a dose uniformity ratio (DUR) target; and
varying the speed at which the conveyor moves the product in the linear direction across the x-ray beam to expose the surface and the additional surfaces to obtain an irradiated product that has a DUR that meets the DUR target.

11. The method of claim 8 wherein varying the speed of the conveyor in the linear direction includes varying the speed in accordance with a speed function, the speed function being a quadratic function of the distance between the position at which the product is irradiated and the reference position.

12. The method of claim 9 wherein varying the speed of the conveyor in the linear direction includes varying the speed in accordance with a speed function, the speed function being a polynomial function of the distance between the position at which the surface of the product is irradiated and the reference position.

* * * * *